(12) United States Patent
Park et al.

(10) Patent No.: US 7,897,163 B2
(45) Date of Patent: Mar. 1, 2011

(54) BONE GRAFT AND SCAFFOLDING MATERIALS IMMOBILIZED WITH OSTEOGENESIS ENHANCING PEPTIDES ON THE SURFACE

(75) Inventors: Yoon Jeong Park, Seoul (KR); Chong-Pyoung Chung, Seoul (KR); Seung Jin Lee, Seoul (KR); Sang Hoon Rhee, Seoul (KR)

(73) Assignee: Seoul National University Industry Foundation (KR)

( * ) Notice: Subject to any disclaimer, the term of this patent is extended or adjusted under 35 U.S.C. 154(b) by 59 days.

(21) Appl. No.: 10/593,430

(22) PCT Filed: Mar. 18, 2005

(86) PCT No.: PCT/KR2005/000801
§ 371 (c)(1),
(2), (4) Date: Sep. 19, 2006

(87) PCT Pub. No.: WO2005/089826
PCT Pub. Date: Sep. 29, 2005

(65) Prior Publication Data
US 2007/0160681 A1    Jul. 12, 2007

(30) Foreign Application Priority Data
Mar. 19, 2004    (KR) .......... 10-2004-0019010

(51) Int. Cl.
*A61K 38/00* (2006.01)
*A61K 38/04* (2006.01)
*A61K 38/16* (2006.01)
*A61K 38/17* (2006.01)
*A61K 38/18* (2006.01)

(52) U.S. Cl. ............ 424/422; 514/7.6; 514/8.8; 514/8.9; 514/9.1; 514/16.7; 514/19.1; 514/20.6; 514/1.1

(58) Field of Classification Search .......... None
See application file for complete search history.

(56) References Cited

U.S. PATENT DOCUMENTS

| | | | |
|---|---|---|---|
| 5,266,683 A * | 11/1993 | Oppermann et al. | ......... 530/326 |
| 5,461,034 A | 10/1995 | Rodan et al. | |
| 5,942,496 A | 8/1999 | Bonadio et al. | |
| 6,194,380 B1 | 2/2001 | Kitamura et al. | |
| 6,280,760 B1 | 8/2001 | Meyer et al. | |
| 6,316,003 B1 * | 11/2001 | Frankel et al. | ........... 424/196.11 |
| 6,409,764 B1 * | 6/2002 | White et al. | ............... 623/16.11 |
| 6,617,307 B1 | 9/2003 | Nishimura et al. | |
| 2005/0064007 A1 | 3/2005 | Steinemann et al. | |

FOREIGN PATENT DOCUMENTS

| | | |
|---|---|---|
| CN | 1304711 A | 7/2001 |
| JP | 05502998 A2 | 5/1993 |
| JP | 08511696 A | 12/1996 |
| JP | 2000506738 A | 9/1997 |
| JP | 07504680 B2 | 6/1999 |
| JP | 2001512344 A1 | 8/2001 |
| JP | 2001526570 A | 12/2001 |
| JP | 2005526541 A | 9/2005 |
| KR | 10-2001-55742 A1 | 7/2001 |
| WO | 9105036 A2 | 4/1991 |
| WO | 9426321 A1 | 11/1994 |
| WO | 9735000 A1 | 9/1997 |
| WO | 9836782 A2 | 8/1998 |
| WO | 02056905 A2 | 7/2002 |
| WO | 03059407 A1 | 7/2003 |
| WO | WO 2005/113585 A2 * | 12/2005 |

OTHER PUBLICATIONS

Puleo et al., 2002, Biomaterials 23:2079-2087.*
Gauvreau et al., 2004, Bioconjugate Chem. 15:1146-1156.*

* cited by examiner

*Primary Examiner* — Elizabeth C. Kemmerer
(74) *Attorney, Agent, or Firm* — Kelly K. Reynolds; Steven J. Hultquist; Intellectual Property/Technology Law

(57) ABSTRACT

The present invention relates to a bone graft material and a scaffold for tissue engineering applications, which have an osteogenesis-promoting peptide immobilized on the surface. More particularly, the invention relates to a bone graft material and a scaffold for tissue engineering applications, which have a cell adhesion-inducing peptide and/or tissue growth factor-derived peptide immobilized on the surface. By the osteogenesis-promoting peptide immobilized on the surface, the inventive bone graft material and scaffold for tissue engineering applications can promote the transition, proliferation and differentiation of cells associated with regeneration, and eventually maximize the regeneration of tissue. Moreover, the peptide immobilized on the surface has low molecular weight, indicating a reduced risk of immune responses upon its application in the body, and can be present in a stable form within the body, thus showing lasting effects. Accordingly, the peptide makes it expedient to perform surgical operations for the regeneration of periodontal tissue, alveolar bone and other bone tissues, and will show high therapeutic effect.

10 Claims, 4 Drawing Sheets

A)

B)

A)

B)

C)

A)

B)

BONE GRAFT AND SCAFFOLDING MATERIALS IMMOBILIZED WITH OSTEOGENESIS ENHANCING PEPTIDES ON THE SURFACE

CROSS-REFERENCE TO RELATED APPLICATIONS

This application is filed under the provisions of 35 U.S.C. §371 and claims the priority of International Patent Application No. PCT/KR2005/000801 filed Mar. 18, 2005, which in turn claims the priority of Korean Patent Application No. 10-2004-0019010 filed Mar. 19, 2004. The disclosures of said International Patent Application and Korean Patent Application are incorporated herein by reference, in their respective entireties, for all purposes.

TECHNICAL FIELD

The present invention relates to a bone graft material and a scaffold for tissue engineering applications, which have osteogenesis-promoting peptides immobilized on the surface, and more particularly, to a bone graft material and a scaffold for tissue engineering applications (hereinafter, referred to as scaffold), which have a cell adhesion-inducing peptide and/or tissue growth factor-derived peptide immobilized on the surface.

BACKGROUND ART

Periodontal tissue that supports teeth consists generally of the alveolar bone, the periodontal ligament tissue forming the periodontal membrane between the alveolar bone and the teeth, and the connective tissue. The loss of alveolar bone caused by the progression of periodontitis involves the loss of periodontal ligament tissue, and at sites with the loss of periodontal ligament tissue, the normal repair of alveolar bone and periodontal ligament tissue after the treatment of periodontitis becomes impossible due to excessive growth of connective tissue. Also, even when new bone is formed, the periodontal ligament tissue will not be normally differentiated so that the loss of tooth function can be caused.

To solve such problems, an attempt to induce the complete regeneration or new formation of tissue using an artificial barrier membrane together with autografting in guided periodontal regeneration is actively made. Also, for the regeneration of bone tissue, a tissue engineering scaffold is used as a bone graft material. Since cases showing the effective induction of periodontal tissue and bone tissue by the introduction of bone graft materials and scaffolds (Camelo, M. et. al, *International J. Periodont. Restorative Dent.* 21:109, 2001) were reported for recent ten years, various materials, including bone powder particles made of bovine bone, have been used as bone materials and tissue engineering scaffolds for tissue regeneration.

Meanwhile, in order to improve the efficiency of such bone graft materials and scaffolds for tissue regeneration, studies to attach materials capable of improving tissue regeneration to the bone graft materials and the scaffolds are now conducted. Among such materials, extracellular matrices or specific tissue growth factors are reported to be excellent in the ability of the repair and regeneration of damaged tissue, and their excellent ability to regenerate tissue was also shown in the results of actual clinical tests.

However, there have been drawbacks that most of the extracellular matrices and growth factors are relatively expensive and are unstable in high-molecular weight living bodies having a molecular weight of several tens kDa, leading to a reduction in the activity. Particularly, there have been problems that they disappear in a few minutes so that they should be administered at high dose to achieve the desired therapeutic effect and thus, cause side effects.

Recently, there have been attempts to reduce shortcomings with a simple application of these materials by adding the tissue growth factors to bone graft materials used in guided bone regeneration and polymer scaffolds used in tissue engineering so as to induce sustained release of the tissue growth factors. Also, some effects of such attempts were proved. However, there is a disadvantage in that, with these bone graft materials or scaffolds themselves, the tissue growth factors are physically mixed, so that, in initial application, the burst release of the growth factors occur, thus making it difficult to maintain the tissue growth factors at an effective concentration for a treatment period.

DISCLOSURE OF INVENTION

Accordingly, the present inventors have made extensive efforts to solve the above-described problems occurring in the prior art, and consequently found that a bone graft material and scaffold having a surface immobilized with the active site peptides of a tissue growth factor and an extracellular matrix protein, which can achieve a tissue regeneration effect, show stable and lasting pharmacological effects, even when a low concentration dose level of the peptides are adhered thereto. On the basis of this finding, the present has been completed.

An object of the present invention is to provide a bone graft material and a scaffold for tissue engineering applications, which can achieve the desired tissue regeneration effect even with low concentration dose levels of cell adhesion-inducing peptide and/or tissue growth factor-derived peptide.

To achieve the above object, the present invention provides a bone graft material and a scaffold for tissue engineering applications, which have a cell adhesion-inducing peptide and/or tissue growth factor-derived peptide immobilized on the surface.

Specifically, the present invention provides a bone graft material and a scaffold, on the surfaces of which a cell adhesion-inducing peptide and/or tissue growth factor-derived peptide having pharmacological activity are immobilized so that the bone graft material and the scaffold have pharmacological activity, whereby their efficiency for the regeneration of bone tissue or other tissues can be increased.

The cell adhesion-inducing peptide or the tissue growth factor-derived peptide is obtained by isolating and extracting the active-site amino acid sequence of physiologically active cytokine and subjecting the extract to chemical modification so as to maintain its active structure.

Specifically, the cell adhesion-inducing peptide is preferably a peptide having an amino acid sequence of RGD. More preferably, it is CGGRGDS (SEQ ID NO: 1) or CGGVACD-CRGDCFC (SEQ ID NO: 2) designed to maintain the structural stability of the amino acid sequence of RGD.

Furthermore, the tissue growth factor-derived peptide is a peptide identified and chemically synthesized from the active site of the tissue growth factor. Preferably it is at least one peptide selected from the group consisting of the following peptides:

(a) the amino acid sequence at positions 2-18 of each of bone morphogenetic proteins (BMP)-2, 4 and 6 [SEQ ID NO: 3 for BMP-2, SEQ ID NO: 4 for BMP-4, and SEQ ID NO: 5 for BMP-6]; the amino acid sequence at positions 24-40 of BMP-2 (SEQ ID NO: 6), the amino acid sequence at positions 47-71 (SEQ ID NO: 7), the amino acid sequence at positions 73-92 (SEQ ID NO: 8), the amino acid sequence at positions 88-105 (SEQ ID NO: 9), the amino acid sequence at positions 283-302 (SEQ ID NO: 10), the amino acid sequence at positions 355-374 (SEQ ID NO: 11) and the amino acid sequence at positions 370-390 (SEQ ID NO: 12); the amino acid sequence at positions 74-93 of BMP-4 (SEQ ID NO: 13), the amino acid sequence at positions 293-313 (SEQ ID NO: 14), the amino acid sequence at positions 366-386 (SEQ ID NO: 15) and the amino acid sequence at positions 382-402 (SEQ ID NO: 16); the amino acid sequence at positions 91-110 of BMP-6 (SEQ ID NO: 17), the amino acid sequence at positions 397-418 (SEQ ID NO: 18), the amino acid sequence at positions 472-490 (SEQ ID NO: 19) and the amino acid sequence at positions 487-510 (SEQ ID NO: 20); and the amino acid sequence at positions 98-117 of BMP-7 (SEQ ID NO: 21), the amino acid sequence at positions 320-340 (SEQ ID NO: 22), the amino acid sequence at positions 390-409 (SEQ ID NO: 23) and the amino acid sequence at positions 405-423 (SEQ ID NO: 24);

(b) the amino acid sequence at positions 62-69 of bone sialoprotein (SEQ ID NO: 25), the amino acid sequence at positions 139-148 (SEQ ID NO: 26), the amino acid sequence at positions 259-277 (SEQ ID NO: 27), the amino acid sequence at positions 199-204 (SEQ ID NO: 28), the amino acid sequence at positions 151-158 (SEQ ID NO: 29), the amino acid sequence at positions 275-291 (SEQ ID NO: 30), the amino acid sequence at positions 20-28 (SEQ ID NO: 31), the amino acid sequence at positions 65-90 (SEQ ID NO: 32), the amino acid sequence at positions 150-170 (SEQ ID NO: 33) and the amino acid sequence at positions 280-290 (SEQ ID NO: 34);

(c) the amino acid sequence at positions 242-250 of a transforming growth factor (SEQ ID NO: 35), the amino acid sequence at positions 279-299 (SEQ ID NO: 36) and the amino acid sequence at positions 343-361 (SEQ ID NO: 37);

(d) the amino acid sequence at positions 100-120 of a platelet-derived growth factor (SEQ ID NO: 738) and the amino acid sequence at positions 121-140 (SEQ ID NO: 39);

(e) the amino acid sequence at positions 23-31 of an acidic fibroblast growth factor (SEQ ID NO: 40) and the amino acid sequence at positions 97-105 (SEQ ID NO: 41);

(f) the amino acid sequence at positions 16-27 of a basic fibroblast growth factor (SEQ ID NO: 42), the amino acid sequence at positions 37-42 (SEQ ID NO: 43), the amino acid sequence at positions 78-84 (SEQ ID NO: 44) and the amino acid sequence at positions 107-112 (SEQ ID NO: 45);

(g) the amino acid sequence at positions 255-275 of dentin sialoprotein (SEQ ID NO: 46), the amino acid sequence at positions 475-494 (SEQ ID NO: 47) and the amino acid sequence at positions 551-573 (SEQ ID NO: 48);

(h) the amino acid sequence at positions 63-83 of a heparin binding EGF-like growth factor (SEQ ID NO: 49), the amino acid sequence at positions 84-103 (SEQ ID NO: 50), the amino acid sequence at positions 104-116 (SEQ ID NO: 51) and the amino acid sequence at positions 121-140 (SEQ ID NO: 52);

(i) the amino acid sequence at positions 326-350 of the cadherin EGF LAG seven-pass G-type receptor 3 (SEQ ID NO: 53), the amino acid sequence at positions 351-371 (SEQ ID NO: 54), the amino acid sequence at positions 372-400 (SEQ ID NO: 55), the amino acid sequence at positions 401-423 (SEQ ID NO: 56), the amino acid sequence at positions 434-545 (SEQ ID NO: 57), the amino acid sequence at positions 546-651 (SEQ ID NO: 58), the amino acid sequence at positions 1375-1433 (SEQ ID NO: 59), the amino acid sequence at positions 1435-1471 (SEQ ID NO: 60), the amino acid sequence at positions 1475-1514 (SEQ ID NO: 61), the amino acid sequence at positions 1515-1719 (SEQ ID NO: 62), the amino acid sequence at positions 1764-1944 (SEQ ID NO: 63) and the amino acid sequence at positions 2096-2529 (SEQ ID NO: 64); and (j) the amino acid sequence at positions 54-159 of an osteoblast specific cadherin (OB-cadherin) (SEQ ID NO: 65), the amino acid sequence at positions 160-268 (SEQ ID NO: 66), the amino acid sequence at positions 269-383 (SEQ ID NO: 67), the amino acid sequence at positions 384-486 (SEQ ID NO: 68) and the amino acid sequence at positions 487-612 (SEQ ID NO: 69).

More preferably, the N-terminal end of the peptide has an addition of a spacer (CGG-) consisting of cysteine and two glycines so as to facilitate chemical immobilization of the peptide to the bone graft material and the scaffold.

The active peptides according to the present invention are obtained by synthesizing each of sequences of 10-20 amino acids in the total amino acid sequence of the tissue growth factor, subjecting the synthesized amino acid sequences to cell adhesion tests to select amino acid sequences having the highest activity, and subjecting the terminal end of the selected amino acid sequences to chemical modification so as to facilitate the immobilization of the modified amino acid sequences to the bone graft material and the scaffold. Thus, the bone graft material can maintain activity only with a sequence of minimum amino acids on the surface while reducing the loss and side effects of the tissue growth factor caused by the physical incorporation and application of the drug, thus providing additional advantages to therapeutic effects.

In the present invention, all kinds and types of bone graft materials and scaffolds can be used if they are used in the technical field. Preferred examples of these bone graft materials and scaffolds include organism-derived bone mineral powders and porous blocks originated from autogeneous bone, bovine bone and porcine bone, synthetic hydroxyapatite powders and porous blocks, tricalcium phosphate powders and porous blocks, monocalcium phosphate powders and porous blocks, bone graft materials made of silicon dioxide (silica), bone-packing graft materials made of a mixture of silica and polymer, fine particles and porous scaffolds made of biocompatible polymers, including chitosan and polylactic acid, and titanium and three-dimensional scaffolds. In this respect, the surface of the bone graft materials and scaffolds is preferably modified so as to facilitate the adhesion of the active peptide to the surface. The scaffolds for tissue engineering applications according to the present invention include barrier membranes, tooth implants and the like which are used for the regeneration of periodontal bone.

Preferred examples of the barrier membranes include, but art not limited to, porous membranes made of polylactic acid, regeneraton membranes made of nanofibers of chitin or chitosan, and film-shaped barrier membranes made of chitin or chitosan. Also, as the implants, titanium implants are preferably used but are not limited thereto. In this respect, the surface of the implants is preferably modified by oxidation and nitrification so as to facilitate the adhesion of the active peptide to the surface.

The peptides according to the present invention are not more sensitive to in vivo enzymatic reactions than the tissue growth factor itself and have a lower in vivo immunogenicity. When the active peptides are immobilized on the surface of bone graft materials, scaffolds, barrier membranes or implants for tissue regeneration and used in surgical operations, the desired concentration of the active peptides can be locally present while showing activity, so that their therapeutic effects can be increased. Thus, the active peptides have suitable characteristics for the regeneration and repair of bone tissue and periodontal tissue.

The inventive peptides having free amino groups or cysteines at the N-terminal end are easy to immobilize on the surface of bone graft materials and scaffolds by crosslinkers. Crosslinkers suitable for use in the present invention include, but are not limited to, 1,4-bis-maleimidobutane (BMB), 1,11-bis-maleimido tetraethyleneglycol (BM[PEO]$_4$), 1-ethyl-3-[3-dimethyl aminopropyl]carbodiimide hydrochloride (EDC), succinimidyl-4-[N-maleimido methylcyclohexane-1-carboxy-[6-amidocaproate]] (SMCC) and sulfo-SMCC, succimidyl 6-[3-(2-pyridyldithio)-ropionamido]hexanoate] (SPDP) and sulfo-SPDP), m-maleimidobenzoyl-N-hydroxysuccinimide ester (MBS) and sulfo-MBS, succimidyl[4-(p-maleimidophenyl)butyrate] (SMPB) and sulfo-SMPB. In addition, the peptides are chemically bound to the surface of bone graft materials and scaffolds so that they are immobilized on the surface in an amount of preferably 0.1-10 mg/cm$^2$, and more preferably 1-5 mg/cm$^2$.

BRIEF DESCRIPTION OF DRAWINGS

In FIG. 1, (A) shows the results of electronic surface analysis of a bone graft material having no peptide immobilized on the surface, and (B) shows the results of electronic surface analysis of a bone graft material having sulfur-containing peptides immobilized on the surface.

In FIG. 2, (A) shows the adhesion pattern of cells to a bone graft surface having no immobilized peptides, and (B) and (C) show the adhesion patterns of cells on bone graft surfaces with immobilized peptides derived from BMP and bone sialoprotein, respectively.

In FIG. 5, (A) shows the bone regeneration ability of a bone graft material (HA) with no immobilized peptide at rabbit cranial defects, and (B) shows the bone regeneration ability of the inventive bone graft material (HA) with immobilized peptides at rabbit cranial defects. New Bone represents bone produced by peptides immobilized on the surface of the bone graft material.

DETAILED DESCRIPTION OF THE INVENTION

Figure 1:
FIG. 1 shows the results of electronic surface analysis of peptides immobilized on bone graft materials according to the present invention.
Figure 1:
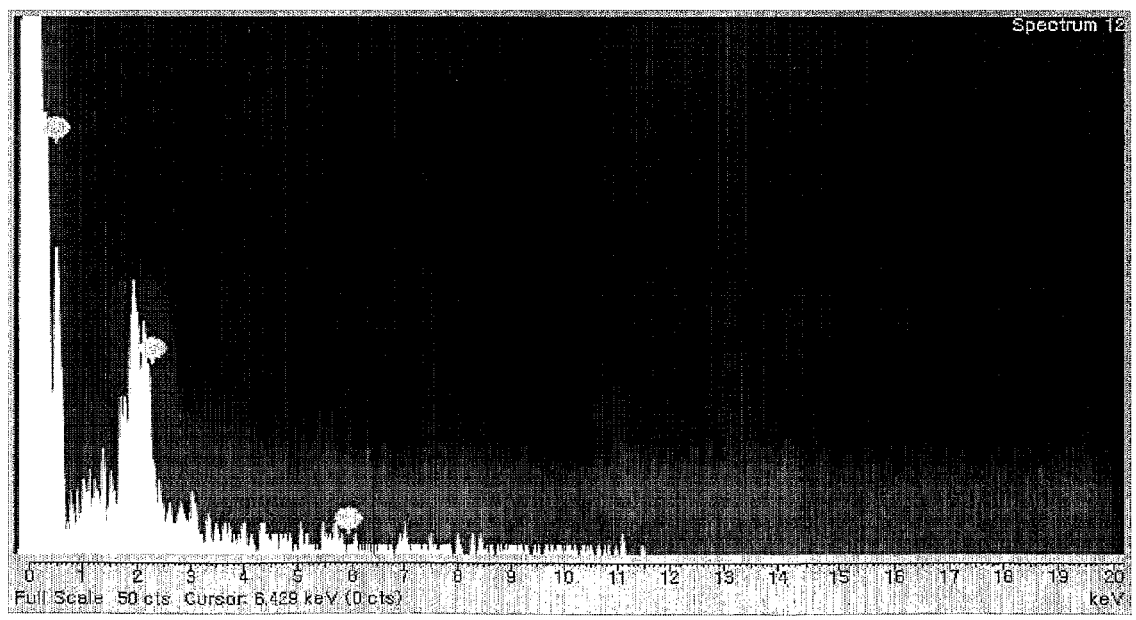

Hereinafter, the present invention will be described in further detail by examples. It will however be obvious to a person skilled in the art that these examples are provided for illustrative purpose only and are not construed to limit the scope of the present invention.

Example 1

Immobilization of Cell Adhesive RGD Peptides on Bovine Bone-Derived Bone Mineral Particles Bovine bone-derived bone mineral particles were washed with ethanol under reduced pressure and then left to stand in a vacuum oven at 100° C. for 20 hours so as to remove impurities from the surface. The surface of the bone mineral particles was treated with a solution of 3-aminopropyl ethoxysilane (APTES) dissolved in hexane, followed by washing. This resulted in the formation of amine residues on the surface, to which crosslinker BMB was then added and bound. The crosslinker-bound bone mineral particles were allowed to react with peptides of SEQ ID NO: 1 and SEQ ID NO: 2 for 12 hours, followed by washing. This yielded the bone mineral particles having the peptides immobilized on the surface.

Example 2

Immobilization of Cell Adhesive RGD Peptides on Synthetic Hydroxyapatite and Tricalcium Phosphate Bone graft powders of synthetic hydroxyapatite and tricalcium phosphate were washed with ethanol under reduced pressure and then left to stand in a vacuum oven at 100° C. so as to remove impurities from the surface. The surface of the bone mineral particles was treated with a solution of 3-aminopropyl ethoxysilane (APTES) in hexane, followed by washing. This resulted in the formation of amine residues on the surface, to which crosslinker BMB was then added and bound. The bone mineral particles with the bound crosslinker were allowed to react with peptides of SEQ ID NO: 1 and SEQ ID NO: 2 for 12 hours, followed by washing. This yielded the bone mineral particles having the peptides immobilized on the surface.

Example 3

Immobilization of Cell Adhesive RGD Peptides on Bone Graft Material of Chitosan

A bone graft material of chitosan prepared in the form of a powdery or porous scaffold was added to 2 ml of phosphate buffer (pH 7.4) to hydrate the surface. To this solution, sulfo-SMCC as a crosslinker was added at a concentration of 5 mg/ml, and the mixture was stirred for 2 hours to introduce functional groups on the surface of the chitosan bone graft material. After 2 hours of reaction at ambient temperature, the chitosan bone graft material was washed and allowed to react with a solution 10 mg of a peptide of SEQ ID NO: 1 dissolved in 100 μl of phosphate buffer for 24 hours. Then, the reaction was washed, thus yielding the chitosan bone graft material with the peptide immobilized thereon.

Example 4

Immobilization of Cell Adhesive RGD Peptide on Bone Graft Material on Bone Graft Material of Polylactic Acid A grafting powder or porous scaffold of polylactic acid were added to phosphate buffer (pH 4.7) to hydrate the surface, followed by reaction with 20 mg/ml of cystamine hydrochloride solution. To this solution, EDC was added dropwise to activate the carboxylic acid on the surface of the bone graft material. The mixture was reacted for 24 hours, washed, and allowed to react with 1 ml of dithiothreniol (DTT) solution (30 mg/ml) for 24 hours so as to introduce sulfhydryl groups onto the surface of the polylactic acid. The modified polylactic acid grafting material was mixed with a cell adhesive RGD peptide (SEQ ID NO: 1) so as to induce S—S bonds between the sulfhydryl groups of the bone grafting material and the peptides, thus immobilizing the peptides on the grafting material.

Example 5

Immobilization of Tissue Growth Factor-Derived Peptides on Bone Mineral Particles For use as tissue growth factor-derived peptides in this Example, peptides were chemically synthesized by adding a CGG spacer to the N-terminal end of each of amino acid sequences of SEQ ID NO: 3 and SEQ ID NOS: 6-9, which contain the cell adhesion and activation domain of bone morphogenetic protein BMP-2 so as to introduce cysteine into the N-terminal end.

Bovine bone-derived bone mineral particles were washed with ethanol under reduced pressure and then left to stand in a vacuum oven at 100° C. for 20 hours so as to remove impurities from the surface. The surface of the bone mineral particles was treated with a solution of 3-aminopropyl ethoxysilane (APTES) in hexane, followed by washing. This resulted in the formation of amine residues on the surface of particles, to which sulfo-SMCC as a crosslinker was then added at a concentration of 5 mg/ml. This mixture was stirred for 2 hours so as to introduce functional groups onto the surface of the bone graft material. After 2 hours of reaction at ambient temperature, the bone graft material was washed, and allowed to react with a solution of 10 mg of the peptides dissolved in 100 µl of phosphate buffer for 24 hours, followed by washing. This yielded the bone mineral particles with the peptides immobilized thereon.

Example 6

Immobilization of Tissue Growth Factor-Derived Peptides on Particles of Synthetic Bone Graft Material In this Example, the same peptides as used in Example 5 used as tissue growth factor-derived peptides. As synthetic bone graft materials, mineral particles of synthetic hydroxyapatite and tricalcium phosphate were washed with ethanol under reduced pressure and stored in a vacuum oven at 100° C. for 20 hours so as to remove impurities from the surface. The surface of the particles was treated with a solution of 3-aminopropyl ethoxysilane (APTES) in hexane, followed by washing. This resulted in the formation of amine residues on the surface, to which 5 mg/ml of sulfo-SMCC as a crosslinker was added. The mixture was stirred for 2 hours to introduce functional groups onto the surface of the bone graft material. After 2 hours of reaction at ambient temperature, the bone graft material was washed, and allowed to react with a solution of 10 mg of the peptides dissolved in 100 µl of phosphate buffer for 24 hours, followed by washing. This yielded the bone graft particles with the tissue growth factor-derived peptides immobilized thereon.

Example 7

Immobilization of Tissue Growth Factor-Derived Peptides on Bone Graft Material and Scaffold of Chitosan A bone graft material and scaffold made of chitosan was added to 2 ml of phosphate buffer (pH 7.4) so as to hydrate the surface, to which crosslinker sulfo-SMCC was added at a concentration of 5 mg/ml. The mixture was stirred for 2 hours so as to introduce functional groups onto the surface of the chitosan bone graft material. After 2 hours of reaction at ambient temperature, the chitosan bone graft material was washed, and allowed to react with a solution of 10 mg of the tissue growth factor-derived peptide of Example 5 dissolved in 100 µl of phosphate buffer, followed by washing. This yielded the chitosan bone graft material and scaffold having the peptide immobilized thereon.

Example 8

Immobilization of Tissue Growth Factor-Derived Peptide on Bone Graft Material and Scaffold of Polylactic Acid A bone grafting powder or porous scaffold of polylactic acid was added to phosphate buffer (pH 4.7) to hydrate the surface and allowed to react with 20 mg/ml of cystamine hydrochloride solution. To the reaction mixture, crosslinker EDC was added dropwise to activate the carboxylic acids on the surface of the polylactic acid bone graft material. After 24 hours of reaction, the resulting material was washed, and allowed to react with 1 ml of dithiothreniol (DTT) solution (30 mg/ml) for 24 hours so as to introduce sulfhydryl groups onto the surface of the polylactic acid. The bone graft material was mixed with a tissue growth factor-derived peptide of SEQ ID NO: 8 having a CGG spacer bound thereto, so as to spontaneously induce a S—S bond between the bone graft material and the peptide, thus immobilizing the peptide on the bone graft material.

Example 9

Immobilization of Bone Sialoprotein-Derived Peptides on Bone Mineral Particles

For use as bone sialoprotein-derived peptides in this Example, a peptide of SEQ ID NO: 15, a peptide including an active domain structure for the induction of calcification, and a peptide of SEQ ID NO: 27 including a cell adhesion functional site, were chemically synthesized.

Bovine bone-derived bone mineral particles were washed with ethanol under reduced pressure and then left to stand in a vacuum oven at 100° C. for 20 hours so as to remove impurities from the surface. The surface of the bone mineral particles was treated with a solution of 3-aminopropyl ethoxysilane (APTES) in hexane, followed by washing. This resulted in the formation of amine residues on the surface, to which 5 mg/ml of crosslinker Sulfo-SMCC was then added. The mixture was stirred for 2 hours so as to functional groups onto the surface of the bone graft material. After reaction, the bone graft material was washed, and allowed to react with a solution of 10 mg of the bone sialoprotein-derived peptides dissolved in 100 µl of phosphate buffer for 24 hours, followed by washing. This yielded the bone mineral particles having the peptides immobilized thereon.

Example 10

Immobilization of Bone Sialoprotein-Derived Peptides on Synthetic Bone Graft Particles In this Example, the same peptides as used in Example 9 were used. Hydroxyapatite and tricalcium phosphate mineral particles were washed with ethanol under reduced pressure and then left to stand in a vacuum oven at 100° C. for 20 hours so as to remove impurities from the surface. The surface of the particles was treated with a solution of 3-aminopropyl ethoxysilane (APTES) in hexane, followed by washing. This resulted in the formation of amine residues on the surface, to which 5 mg/ml of crosslinker sulfo-SMCC was then added. The mixture was stirred for 2 hours so as to introduce functional groups onto the surface of the bone graft material. After completion of the reaction, the bone graft material was washed, to which a solution of 10 mg of the same peptides as used in Example 9, which have been dissolved in 100 µl of phosphate buffer, was added and allowed to react for 24 hours. The reaction product was washed, thus yielding the bone graft material having the peptides immobilized thereon.

Example 11

Immobilization of Peptides Containing Adhesion and Activation Sites of Bone Sialoprotein on Bone Graft Material of Chitosan In this Example, the same peptides as used in Example 9 were used. A bone graft material and scaffold of chitosan were added to 2 ml of phosphate buffer (pH 7.4) to hydrate the surface. To this solution, 5 mg/ml of crosslinker sulfo-SMCC was added and stirred for 2 hours to introduce functional groups onto the surface of bone graft material. After completion of the reaction, the chitosan bone graft material was washed, to which a solution of 10 mg of the peptides dissolved in 100 µl of phosphate buffer was added and allowed to react for 24 hours, followed by washing. This yielded the chitosan bone graft material and scaffold having the peptides immobilized thereon.

Example 12

Immobilization of Peptides Containing Adhesion and Activation Sites of Bone Sialoprotein on Bone Graft Material and Scaffold of Polylactic Acid In this Example, the same peptides as used in Example 9 were used. A bone graft material and scaffold of polylactic acid were added to phosphate buffer (pH 4.7) so as to hydrate the surface, and then allowed to react with 20 mg/ml of cystamine hydrochloride solution. To the reaction mixture, crosslinker EDAC was added dropwise to activate the carboxylic acids on the surface of the polylactic acid. After 24 hours of reaction, the reaction product was washed, to which 1 ml of DTT solution (30 mg/ml) was added and allowed to react for 24 hours so as to introduce sulfhydryl groups onto the surfaces of the bone graft material and the scaffold. The bone graft material and the scaffold were mixed with the peptides so as to spontaneously induce S—S bonds between the bond graft material and the peptides, thus immobilizing the peptides on the bone graft material.

Example 13

Immobilization of Osteogenesis-Promoting Peptides on Barrier Membrane of Chitosan A barrier membrane of chitosan was added to 2 ml of phosphate buffer (pH 7.4) to hydrate the surface of the barrier membrane. To the solution, 5 mg/ml of crosslinker sulfo-SMCC was added and the mixture was stirred for 2 hours so as to introduce functional groups onto the surface of the barrier membrane. After completion of the reaction, the barrier membrane was washed, to which a solution of 5 ml of each of a cell adhesion peptide having SEQ ID NO: 1, a BMP-2-derived peptide used in Example 9, and a bone sialoprotein-derived peptide used in Example 9, which has been dissolved in 100 µl of phosphate buffer, was added and allowed to react for 24 hours. After washing, the barrier membrane having the peptides immobilized thereon was obtained.

Example 14

Immobilization of Osteogenesis-Promoting Peptides on a Barrier Membrane of Polylactic Acid A barrier membrane of polylactic acid was added to phosphate buffer (pH 4.7) so as to hydrate the surface, and is allowed to 20 mg/ml of cystamine hydrochloride solution. To the reaction mixture, crosslinker EDC was added dropwise to activate the carboxylic acids on the surface of the polylactic acid. After 24 hours of reaction, the barrier membrane was washed, to which 1 ml of DTT solution (30 mg/ml) was added and allowed to react for 24 hours so as to introduce sulfhydryl groups onto the surface of the barrier membrane. The resulting barrier membrane was mixed with each of a cell adhesion peptide of SEQ ID NO: 1, a BMP-2-derived peptide used in Example 5 and a bone sialoprotein-derived peptide used in Example 9 so as to spontaneously induce S—S bonds between the barrier membrane and the peptides, thus immobilizing the peptides on the barrier membrane.

Example 15

Immobilization of Osteogenesis-Promoting Peptide on Titanium Implant

The surface of an implant made of titanium was treated with nitrogen plasma so as to form amine groups on the surface. To the implant, 5 mg/ml of crosslinker sulfo-SMCC was added and stirred for 2 hours so as to introduce functional groups onto the surface. After completion of the reaction, the implant was washed, to which a solution of each of 5 ml of a cell adhesion peptide having SEQ ID NO: 1, a BMP-2-derived peptide used in Example 5 and a bone sialoprotein-derived peptide used in Example 9, which has been dissolved in 100 µl of phosphate buffer, was added and allowed to react for 24 hours. The resulting implant was washed, thus the obtaining the implant having the peptides immobilized thereon.

Test Example 1

Analysis of Surface of Bone Graft Materials According to the Present Invention In order to analyze the surface of each of the peptide-immobilized bone graft materials prepared in Examples 1-12, the bone graft materials were fixed with 2% glutaraldehyde solution. The fixed bone graft materials were treated with 1% osmium tetroxide solution, followed by washing, dewatering and drying.

The surface of the prepared bone graft materials was analyzed by an XPS method which determines the presence or absence of bonds by identifying elements immobilized on the surface of a substance. In this respect, the presence or absence of bonds were determined depending on the presence or absence of sulfur since there are disulfide bonds between the bone graft material and the peptides immobilized on the bone graft material according to the present invention.

FIG. 1 shows the results of analysis of peptides immobilized on a bone graft material of chitosan according to the present invention. In FIG. 1, (A) shows the surface of a bone graft material made of chitosan, which has not been modified with peptides, and (B) shows a bone graft material having a sulfur-containing peptide immobilized on the surface. As shown in FIG. 1, the presence of sulfur on the surface of the peptide-immobilized bone graft material was observed, suggesting that the peptides were immobilized. Furthermore, the content of sulfur in the peptide-immobilized bone graft material was measured in order to determine the immobilization rate of the peptide in the total surface area of the bone graft material. As a result, as shown in Table 1 below, sulfur was not detected in the chitosan with no peptide whereas 8.66% of sulfur was detected in the peptide-immobilized chitosan.

TABLE 1

| | Element | | | | | |
|---|---|---|---|---|---|---|
| | O (%) | N (%) | C (%) | S (%) | O/C | N/C |
| Chitosan with no peptide | 31.83 | 6.18 | 61.99 | 0 | 0.513 | 0.0997 |
| Peptide immobilized chitosan | 32.33 | 2.96 | 60.05 | 8.66 | 0.605 | 0.033 |

Test Example 2

Test of Cell Adhesion of Bone Graft Materials According to the Present Invention Osteoblasts ((MC3T3 cell line) were inoculated on the peptide-immobilized bone graft materials prepared in Examples 3, 7 and 11 and then cultured for each of 4 hours and 1 day. The bone graft materials with the cultured osteoblasts were fixed with 2% glutaraldehyde solution. The fixed bone graft materials were added with a fluorescent-labeled phalloidin solution treated with 1% triton X-100, thus staining the cytoplasm. Then, after the samples were washed and fixed, the cells adhered to the bone graft materials were observed with a confocal laser scanning microscope (FIG. 2).

Figure 2:
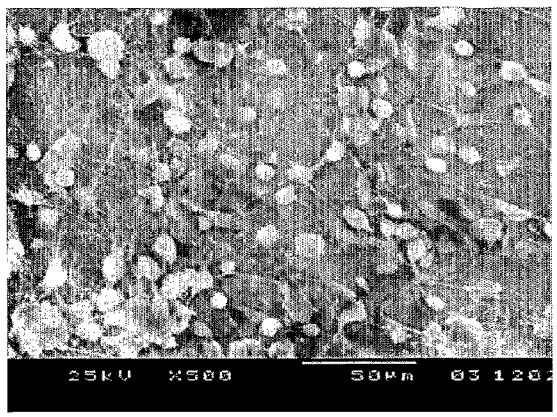
FIG. 2 shows confocal laser scanning microscopic images showing the cell adhesion patterns of the inventive bone graft materials.
Figure 2:
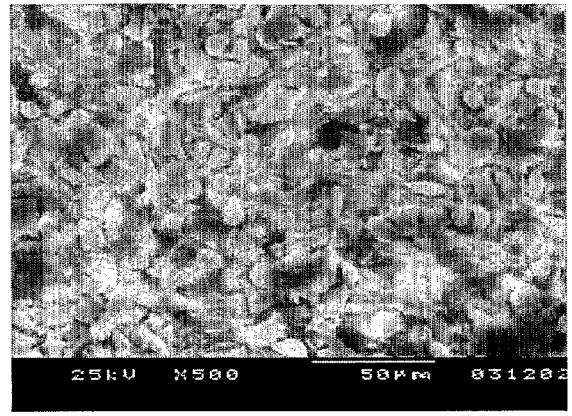
Figure 2:
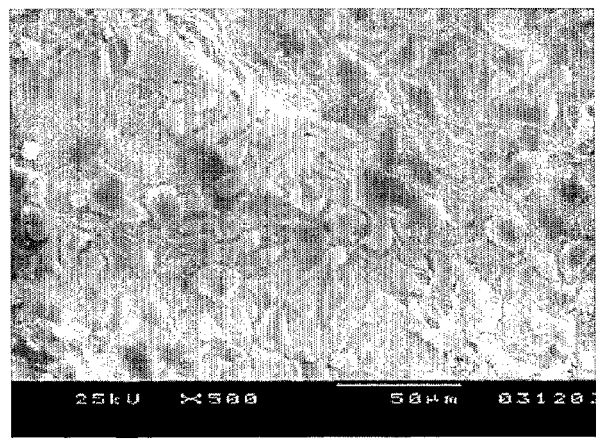

In FIG. 2, (A) shows the cell adhesion to the bone graft material with no peptide, and (B) and (C) show the cell adhesion to the bone graft materials on which the BMP-derived peptide and the bone sialoprotein-derived peptide have been immobilized, respectively. As a result, for the bone graft material with no immobilized peptide, the spherical and unstable adhesion of the cells was observed, whereas on the surfaces of the bone graft materials with the BMP- and bone sialoprotein-derived peptides, the stable adhesion of the cells (including the elongation of the cytoplasm in most of the cells after 4 hours of the cell culture) was observed.

Figure 3:
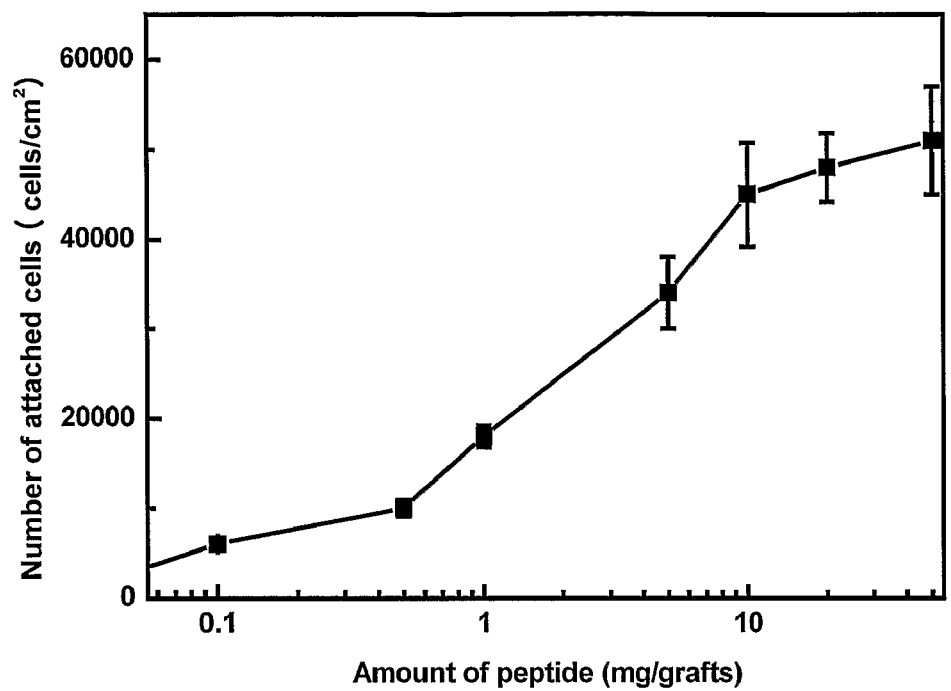
FIG. 3 is a graphic diagram showing the results of quantitative analysis for the adhesion of cells on the inventive bone graft surface with immobilized peptides.

FIG. 3 shows the results of quantitative analysis for the cell adhesion. As shown in FIG. 3, the chitosan bone graft materials modified with the peptides showed a remarkable increase in the adhesion of the cells as compared to the chitosan bone graft material with no immobilized peptide, and this increase was proportional to the amount of the immobilized peptides up to any concentration.

Test Example 3

Expression of Differentiation Marker Proteins in Osteoblasts Cultured on Surface of Peptide-Immobilized Bone Graft Material According to the Present Invention In order to determine the expression of differentiation marker proteins in osteoblasts cultured on the surface of the peptide-immobilized bone graft material according to the present invention, the expression level of differentiation marker proteins smad 1, 5 and 8 was analyzed by Western blot. Osteoblasts were inoculated on the surfaces of the bone graft material and the peptide-immobilized bone graft material and then cultured for 2 weeks. After culturing, total protein in the cells was extracted, and quantified by measuring the absorbance at 280 nm. 2 μl of the protein solution (1 mg/ml) was taken and electrophoresed on acrylamide gel, followed by reaction with an antibody to differentiation marker proteins smad 1, 5 and 8. Then, the protein solution was allowed to react with a labeled secondary antibody, and protein bands appearing by the development of the gel were observed and their density was measured (FIG. 4).

Figure 4:
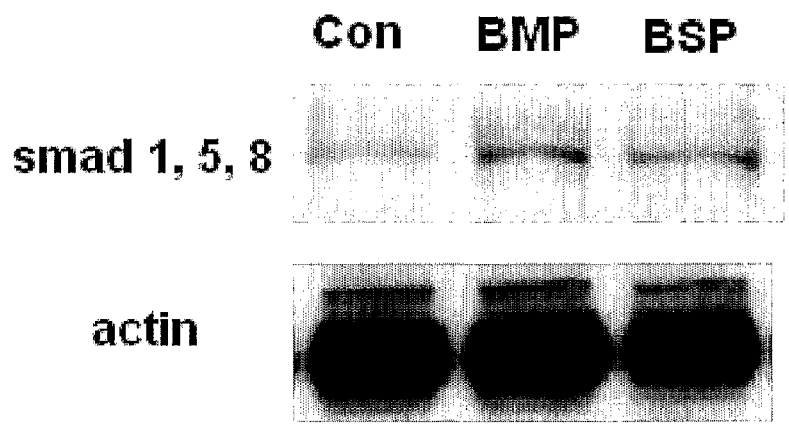
FIG. 4 is a photograph showing the results of Western blot measurement for the amount of bone tissue differentiation markers smad 1, 5, 8 proteins in cells collected after dispensing cells on the inventive bone graft material and culturing the dispensed cells for a given period of time (Con: a bone graft material with no immobilized peptide; BMP: a bone graft material having BMP-derived peptides immobilized thereon; and BSP: a bone graft material having sialoprotein-derived peptides immobilized thereon).

As a result, as shown in FIG. 4, the expression of the smad proteins cultured on the surface of the peptide-immobilized bone graft material was significantly increased as compared to the case of the cells cultured on the bone graft material with no immobilized peptide. This suggests that the cells grown on the surface of the bone graft material having the tissue growth factor-derived peptide immobilized on the surface are differentiated into bone tissue in a facilitated manner.

Test Example 4

Effect of Peptide-Immobilized Bone Graft Material on Rabbit Cranial Regeneration The peptide-immobilized bone graft materials prepared in Examples 1-5 were grafted in rabbit cranial circular defects in order to examine their bone regeneration ability. At the cranial sites of anesthetized rabbits, circular bone defects with a diameter of 8 mm were formed. The bone graft material and the peptide-immobilized bone graft materials were grafted into the bone defects at an amount of 50 mg/defect, and the bone membrane and the skin were double sutured to each other. At 2 weeks after the grafting, the animals were sacrificed, and samples collected from the animals were fixed in formalin solution and then the tissue was embedded so as to prepare samples having a thickness of 20 μm. The prepared samples were stained with basic fuchsine and toluidine blue, thus preparing non-decalcified samples. The prepared samples were photographed with an optical microscope.

Figure 5:
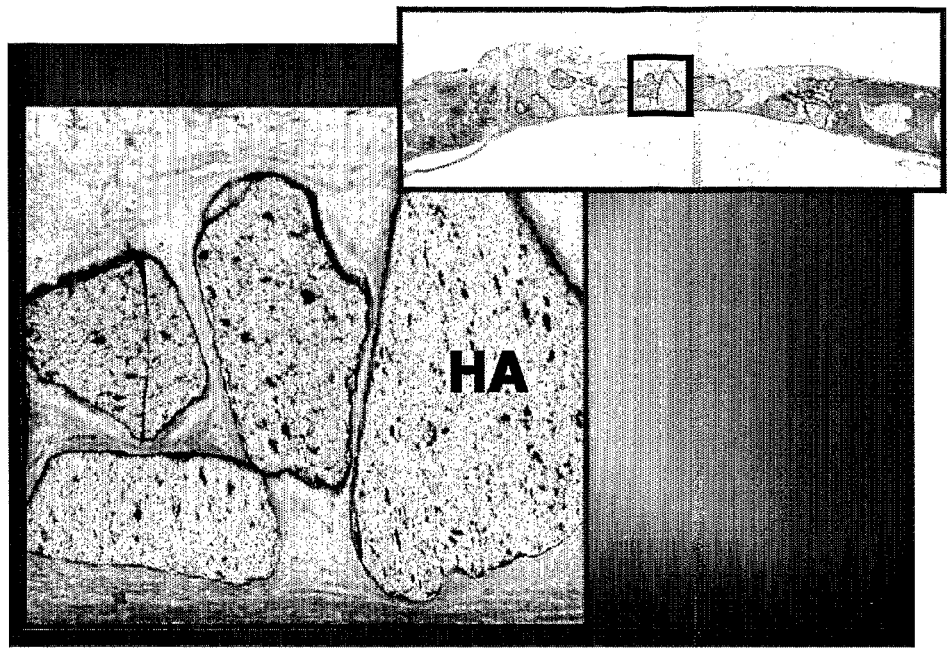
FIG. 5 shows photographs showing the bone regeneration ability of the inventive bone graft materials at rabbit cranial defects.
Figure 5:
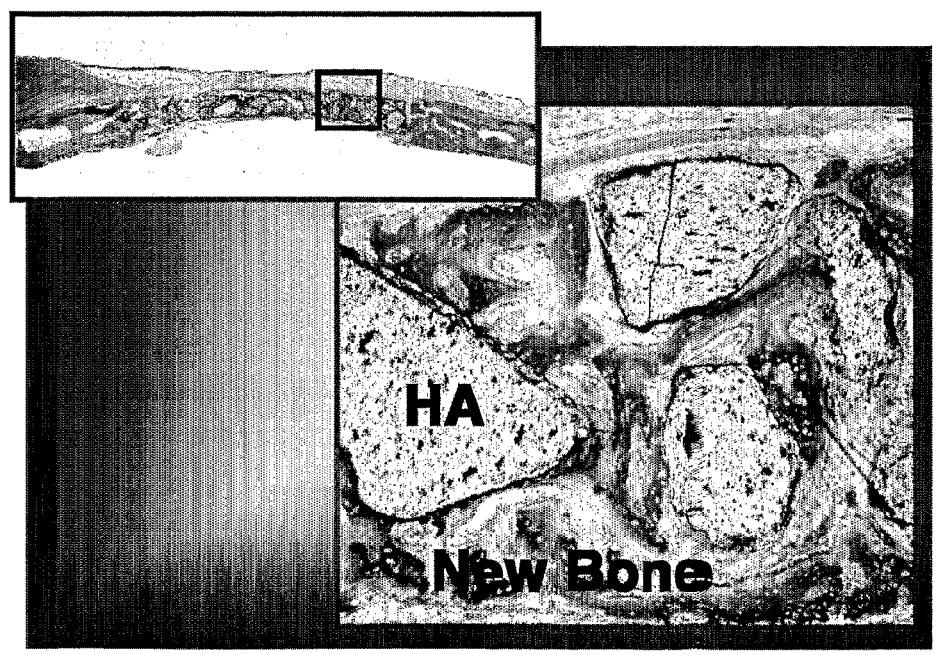

FIG. 5 shows the bone regeneration effect of the peptide-immobilized bone graft materials. As shown in FIG. 5, the inventive bone graft materials having the osteogenesis-promoting peptide adhered to the surface, which have been applied to the rabbit cranial defects (B), showed remarkable bone regeneration ability within 2 weeks as compared to the bone graft material with no peptide (A).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof. Those skilled in the art will appreciate that simple modifications, variations and additions to the present invention are possible, without departing from the scope and spirit of the invention as disclosed in the accompanying claims.

INDUSTRIAL APPLICABILITY

As described above, the present invention provides the bone graft material and scaffold having a surface immobilized with the cell adhesion-inducing peptide and/or the tissue growth factor-derived peptide, which can achieve the desired tissue regeneration effect even at the low concentration dose level.

The inventive bone graft material and the scaffold for tissue engineering applications, have the osteogenesis-promoting peptides immobilized on the surface, can promote the adhesion of cells and the differentiation of cells into bone tissue, and can prevent rapid degradation of a tissue growth factor caused by its simple incorporation according to the prior art, and side effects resulting from its leakage into the body. Moreover, they allow a great reduction in the costs caused by applying a large amount of the tissue growth factor to increase its local concentration.

What is claimed is:

1. A bone graft material having a cell adhesion-inducing peptide and/or tissue growth factor-derived peptide immobilized on a surface thereof, wherein (i) the peptide is immobilized on said surface in an amount of 0.1-10 mg/cm$^2$, (ii) the tissue growth factor-derived peptide has an addition of a CGG spacer at its N-terminal end, (iii) said surface has been modified by oxidation and nitrification to facilitate adhesion of the peptide thereto, and (iv) the cell adhesion-inducing peptide has an amino acid sequence of RGD.

2. The bone graft material according to claim 1, wherein the cell adhesion-inducing peptide has an amino acid sequence of CGGRGDS (SEQ ID NO: 1) or CGGVACD-CRGDCFC (SEQ ID NO: 2).

3. A scaffold for tissue engineering applications, which has a cell adhesion-inducing peptide and/or tissue growth factor-derived peptide immobilized on the surface, wherein the peptide is immobilized on the surface in an amount of 0.1-10 mg/cm$^2$, the tissue growth factor-derived peptide has an addition of CGG spacer at the N-terminal end, the scaffold is an implant, and the surface of the implant is modified by oxidation and nitrification to facilitate the adhesion of the active peptide to the surface.

4. The scaffold for tissue engineering applications according to claim 3, wherein the cell adhesion-inducing peptide has an amino acid sequence of RGD.

5. The scaffold for tissue engineering applications according to claim 4, wherein the cell adhesion-inducing peptide has an amino acid sequence of CGGRGDS (SEQ ID NO: 1) or CGGVACDCRGDCFC (SEQ ID NO: 2).

6. The scaffold for tissue engineering applications according to claim 3, wherein the tissue growth factor-derived peptide is at least one peptide selected from the group consisting of the following peptides: (a) the amino acid sequence at positions 2-18 of each of bone morphogenetic proteins (BMP)-2, 4 and 6 [SEQ ID NO: 3 for BMP-2, SEQ ID NO: 4 for BMP-4, and SEQ ID NO: 5 for BMP-6]; the amino acid sequence at positions 24-40 of BMP-2 (SEQ ID NO: 6), the amino acid sequence at positions 47-71 of BMP-2 (SEQ ID NO: 7), the amino acid sequence at positions 73-92 of BMP-2 (SEQ ID NO: 8), the amino acid sequence at positions 88-105 of BMP-2 (SEQ ID NO: 9), the amino acid sequence at positions 283-302 of BMP-2 (SEQ ID NO: 10), the amino acid sequence at positions 355-374 of BMP-2 (SEQ ID NO: 11) and the amino acid sequence at positions 370-390 of BMP-7 (SEQ ID NO: 12); the amino acid sequence at positions 74-93 of BMP-4 (SEQ ID NO: 13), the amino acid sequence at positions 293-313 of bone sialoprotein (SEQ ID NO: 14), the amino acid sequence at positions 366-386 of BMP-4 (SEQ ID NO: 15) and the amino acid sequence at positions 382-402 of BMP-4 (SEQ ID NO: 16); the amino acid sequence at positions 91-110 of BMP-6 (SEQ ID NO: 17), the amino acid sequence at positions 397-418 of BMP-6 (SEQ ID NO: 18), the amino acid sequence at positions 472-490 of BMP-6 (SEQ ID NO: 19) and the amino acid sequence at positions 487-510 of BMP-6 (SEQ ID NO: 20); and the amino acid sequence at positions 98-117 of BMP-7 (SEQ ID NO: 21), the amino acid sequence at positions 320-340 of BMP-7 (SEQ ID NO: 22), the amino acid sequence at positions 390-409 of BMP-7 (SEQ ID NO: 23) and the amino acid sequence at positions 405-423 of BMP-7 (SEQ ID NO: 24); (b) the amino acid sequence at positions 62-69 of bone sialoprotein (SEQ ID NO: 25), the amino acid sequence at positions 139-148 of bone sialoprotein (SEQ ID NO: 26), the amino acid sequence at positions 259-277 of bone sialoprotein (SEQ ID NO: 27), the amino acid sequence at positions 199-204 of bone sialoprotein (SEQ ID NO: 28), the amino acid sequence at positions 151-158 of bone sialoprotein (SEQ ID NO: 29), the amino acid sequence at positions 275-291 of bone sialoprotein (SEQ ID NO: 30), the amino acid sequence at positions 20-28 of bone sialoprotein (SEQ ID NO: 31), the amino acid sequence at positions 65-90 of bone sialoprotein (SEQ ID NO: 32), the amino acid sequence at positions 150-170 of bone sialoprotein (SEQ ID NO: 33) and the amino acid sequence at positions 280-290 of bone sialoprotein (SEQ ID NO: 34); (c) the amino acid sequence at positions 242-250 of a transforming growth factor (SEQ ID NO: 35), the amino acid sequence at positions 279-299 of a transforming growth factor (SEQ ID NO: 36) and the amino acid sequence at positions 343-361 of a transforming growth factor (SEQ ID NO: 37); (d) the amino acid sequence at positions 100-120 of a platelet-derived growth factor (SEQ ID NO: 38) and the amino acid sequence at positions 121-140 of a platelet-derived growth factor (SEQ ID NO: 39); (e) the amino acid sequence at positions 23-31 of an acidic fibroblast growth factor (SEQ ID NO: 40) and the amino acid sequence at positions 97-105 of an acidic fibroblast growth factor (SEQ ID NO: 41); (f) the amino acid sequence at positions 16-27 of a basic fibroblast growth factor (SEQ ID NO: 42), the amino acid sequence at positions 37-42 of a basic fibroblast growth factor (SEQ ID NO: 43), the amino acid sequence at positions 78-84 of a basic fibroblast growth factor (SEQ ID NO: 44) and the amino acid sequence at positions 107-112 of a basic fibroblast growth factor (SEQ ID NO: 45); (g) the amino acid sequence at positions 255-275 of dentin sialoprotein (SEQ ID NO: 46), the amino acid sequence at positions 475-494 of dentin sialoprotein (SEQ ID NO: 47) and the amino acid sequence at positions 551-573 of dentin sialoprotein (SEQ ID NO: 48); (h) the amino acid sequence at positions 63-83 of a heparin binding EGF-like growth factor (SEQ ID NO: 49), the amino acid sequence at positions 84-103 of a heparin binding EGF-like growth factor (SEQ ID NO: 50), the amino acid sequence at positions 104-116 of a heparin binding EGF-like growth factor (SEQ ID NO: 51) and the amino acid sequence at positions 121-140 of a heparin binding EGF-like growth factor (SEQ ID NO: 52); (i) the amino acid sequence at positions 326-350 of the cadherin EGF LAG seven-pass G-type receptor 3 (SEQ ID NO: 53), the amino acid sequence at positions 351-371 of the cadherin EGF LAG seven-pass G-type receptor 3 (SEQ ID NO: 54), the amino acid sequence at positions 372-400 of the cadherin EGF LAG seven-pass G-type receptor 3 (SEQ ID NO: 55), the amino acid sequence at positions 401-423 of the cadherin EGF LAG seven-pass G-type receptor 3 (SEQ ID NO: 56), the amino acid sequence at positions 434-545 of the cadherin EGF LAG seven-pass G-type receptor 3 (SEQ ID NO: 57), the amino acid sequence at positions 546-651 of the cadherin EGF LAG seven-pass G-type receptor 3 (SEQ ID NO: 58), the amino acid sequence at positions 1375-1433 of the cadherin EGF LAG seven-pass G-type receptor 3 (SEQ ID NO: 59), the amino acid sequence at positions 1435-1471 of the cadherin EGF LAG seven-pass G-type receptor 3 (SEQ ID NO: 60), the amino acid sequence at positions 1475-1514 of the cadherin EGF LAG seven-pass G-type receptor 3 (SEQ ID NO: 61), the amino acid sequence at positions 1515-1719 of the cadherin EGF LAG seven-pass G-type receptor 3 (SEQ ID NO: 62), the amino acid sequence at positions 1764-1944 of the cadherin EGF LAG seven-pass G-type receptor 3 (SEQ ID NO: 63) and the amino acid sequence at positions 2096-2529 of the cadherin EGF LAG seven-pass G-type receptor 3 (SEQ ID NO: 64); and (j) the amino acid sequence at positions 54-159 of an osteoblast specific cadherin (OB-cadherin) (SEQ ID NO: 65), the amino acid sequence at positions 160-268 of an osteoblast specific cadherin (OB-cadherin) (SEQ ID NO: 66), the amino acid sequence at positions 269-383 of an osteoblast specific cadherin (OB-cadherin) (SEQ ID NO: 67), the amino acid sequence at positions 384-486 of an osteoblast specific cadherin (OB-cadherin) (SEQ ID NO: 68) and the amino acid sequence at positions 487-612 of an osteoblast specific cadherin (OB-cadherin) (SEQ ID NO: 69).

7. The scaffold for tissue engineering applications according to claim 3, wherein the implant is titanium implant.

8. The scaffold for tissue engineering applications according to claim 3, wherein the surface is immobilized with a crosslinker.

9. The scaffold for tissue engineering applications according to claim 8, wherein the crosslinker is any one or more selected from the group consisting of 1,4-bis-maleimidobutane (BMB), 1,11-bis-maleimido tetraethyleneglycol (BM[PEO]-4), 1-ethyl-3-[3-dimethyl aminopropyl]carbodiimide hydrochloride (EDC), succinimidyl-4-[N-maleimido methylcyclohexane-1-carboxy-[6-amidocaproate]] (SMCC) and sulfo-SMCC, succinimidyl 6-[3-(2-pyridyldithio)-ropionamido]hexanoate] (SPDP) and sulfo-SPDP), m-maleimidobenzoyl-N-hydroxysuccinimide ester (MBS) and sulfo-MBS, succinimidyl[4-(p-maleimidophenyl)butyrate](SMPB) and sulfo-SMPB.

10. A scaffold for tissue engineering applications, comprising:
    a surface comprising bovine bone-derived mineral particles; and
    one or more peptides comprising the amino acid sequence of SEQ ID NO: 6 immobilized on said surface wherein the immobilization comprises crosslinking with sulfo-SMCC.

* * * * *

```
                          SEQUENCE LISTING

<160> NUMBER OF SEQ ID NOS: 69

<210> SEQ ID NO 1
<211> LENGTH: 7
<212> TYPE: PRT
<213> ORGANISM: Artificial Sequence
<220> FEATURE:
<223> OTHER INFORMATION: RGD containing peptide

<400> SEQUENCE: 1

Cys Gly Gly Arg Gly Asp Ser
1               5

<210> SEQ ID NO 2
<211> LENGTH: 14
<212> TYPE: PRT
<213> ORGANISM: Artificial Sequence
<220> FEATURE:
<223> OTHER INFORMATION: RGD containing peptide

<400> SEQUENCE: 2

Cys Gly Gly Val Ala Cys Asp Cys Arg Gly Asp Cys Phe Cys
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Partial peptide of BMP-2

<400> SEQUENCE: 3

Ala Lys His Lys Gln Arg Lys Arg Leu Lys Ser Ser Cys Lys Arg His
1               5                   10                  15

Pro

<210> SEQ ID NO 4
<211> LENGTH: 17
<212> TYPE: PRT
<213> ORGANISM: Artificial Sequence
<220> FEATURE:
<223> OTHER INFORMATION: Partial peptide of BMP-4

<400> SEQUENCE: 4

Pro Lys His His Ser Gln Arg Ala Arg Lys Lys Asn Lys Asn Cys Arg
1               5                   10                  15

Arg

<210> SEQ ID NO 5
```

```
<211> LENGTH: 17
<212> TYPE: PRT
<213> ORGANISM: Artificial Sequence
<220> FEATURE:
<223> OTHER INFORMATION: Partial peptide of BMP-6

<400> SEQUENCE: 5

Ala Ser Ser Arg Arg Arg Gln Gln Ser Arg Asn Arg Ser Thr Gln Ser
1               5                   10                  15
Gln

<210> SEQ ID NO 6
<211> LENGTH: 17
<212> TYPE: PRT
<213> ORGANISM: Artificial Sequence
<220> FEATURE:
<223> OTHER INFORMATION: Partial peptide of BMP-2

<400> SEQUENCE: 6

Ser Asp Val Gly Trp Asn Asp Trp Ile Val Ala Pro Pro Gly Tyr His
1               5                   10                  15
Ala

<210> SEQ ID NO 7
<211> LENGTH: 25
<212> TYPE: PRT
<213> ORGANISM: Artificial Sequence
<220> FEATURE:
<223> OTHER INFORMATION: Partial peptide of BMP-2

<400> SEQUENCE: 7

Cys Pro Phe Pro Leu Ala Asp His Leu Asn Ser Thr Asn His Ala Ile
1               5                   10                  15
Val Gln Thr Leu Val Asn Ser Val Asn
            20                  25

<210> SEQ ID NO 8
<211> LENGTH: 20
<212> TYPE: PRT
<213> ORGANISM: Artificial Sequence
<220> FEATURE:
<223> OTHER INFORMATION: Partial peptide of BMP-2

<400> SEQUENCE: 8

Lys Ile Pro Lys Ala Cys Cys Val Pro Thr Glu Leu Ser Ala Ile Ser
1               5                   10                  15
Met Leu Tyr Leu
            20

<210> SEQ ID NO 9
<211> LENGTH: 18
<212> TYPE: PRT
<213> ORGANISM: Artificial Sequence
<220> FEATURE:
<223> OTHER INFORMATION: Partial peptide of BMP-2

<400> SEQUENCE: 9

Ser Met Leu Tyr Leu Asp Glu Asn Glu Lys Val Val Leu Lys Asn Tyr
1               5                   10                  15
Gln Asp

<210> SEQ ID NO 10
<211> LENGTH: 20
<212> TYPE: PRT
<213> ORGANISM: Artificial Sequence
```

```
<220> FEATURE:
<223> OTHER INFORMATION: Partial peptide of BMP-2

<400> SEQUENCE: 10

Gln Ala Lys His Lys Gln Arg Lys Arg Leu Lys Ser Ser Cys Lys Arg
1               5                   10                  15

His Pro Leu Tyr
            20

<210> SEQ ID NO 11
<211> LENGTH: 20
<212> TYPE: PRT
<213> ORGANISM: Artificial Sequence
<220> FEATURE:
<223> OTHER INFORMATION: Partial peptide of BMP-2

<400> SEQUENCE: 11

Lys Ile Pro Lys Ala Cys Cys Val Pro Thr Glu Leu Ser Ala Ile Ser
1               5                   10                  15

Met Leu Tyr Leu
            20

<210> SEQ ID NO 12
<211> LENGTH: 21
<212> TYPE: PRT
<213> ORGANISM: Artificial Sequence
<220> FEATURE:
<223> OTHER INFORMATION: Partial peptide of BMP-7

<400> SEQUENCE: 12

Ser Met Leu Tyr Leu Asp Glu Asn Glu Lys Val Val Leu Lys Asn Tyr
1               5                   10                  15

Gln Asp Met Val Val
            20

<210> SEQ ID NO 13
<211> LENGTH: 21
<212> TYPE: PRT
<213> ORGANISM: Artificial Sequence
<220> FEATURE:
<223> OTHER INFORMATION: Partial peptide of BMP-4

<400> SEQUENCE: 13

Ser Ser Ile Pro Lys Ala Cys Cys Val Pro Thr Glu Leu Ser Ala Ile
1               5                   10                  15

Ser Met Leu Tyr Leu
            20

<210> SEQ ID NO 14
<211> LENGTH: 21
<212> TYPE: PRT
<213> ORGANISM: Artificial Sequence
<220> FEATURE:
<223> OTHER INFORMATION: Partial peptide of bone sialoprotein

<400> SEQUENCE: 14

Pro Lys His His Ser Gln Arg Ala Arg Lys Lys Asn Lys Asn Cys Arg
1               5                   10                  15

Arg His Ser Leu Tyr
            20

<210> SEQ ID NO 15
<211> LENGTH: 21
<212> TYPE: PRT
<213> ORGANISM: Artificial Sequence
```

```
<220> FEATURE:
<223> OTHER INFORMATION: Partial peptide of BMP-4

<400> SEQUENCE: 15

Ser Ser Ile Pro Lys Ala Cys Cys Val Pro Thr Glu Leu Ser Ala Ile
1               5                   10                  15

Ser Met Leu Tyr Leu
            20

<210> SEQ ID NO 16
<211> LENGTH: 21
<212> TYPE: PRT
<213> ORGANISM: Artificial Sequence
<220> FEATURE:
<223> OTHER INFORMATION: Partial peptide of BMP-4

<400> SEQUENCE: 16

Ser Met Leu Tyr Leu Asp Glu Tyr Asp Lys Val Val Leu Lys Asn Tyr
1               5                   10                  15

Gln Glu Met Val Val
            20

<210> SEQ ID NO 17
<211> LENGTH: 20
<212> TYPE: PRT
<213> ORGANISM: Artificial Sequence
<220> FEATURE:
<223> OTHER INFORMATION: Partial peptide of BMP-6

<400> SEQUENCE: 17

Tyr Val Pro Lys Pro Cys Cys Ala Pro Thr Lys Leu Asn Ala Ile Ser
1               5                   10                  15

Val Leu Tyr Phe
            20

<210> SEQ ID NO 18
<211> LENGTH: 22
<212> TYPE: PRT
<213> ORGANISM: Artificial Sequence
<220> FEATURE:
<223> OTHER INFORMATION: Partial peptide of BMP-6

<400> SEQUENCE: 18

Val Ser Ser Ala Ser Asp Tyr Asn Ser Ser Glu Leu Lys Thr Ala Cys
1               5                   10                  15

Arg Lys His Glu Leu Tyr
            20

<210> SEQ ID NO 19
<211> LENGTH: 20
<212> TYPE: PRT
<213> ORGANISM: Artificial Sequence
<220> FEATURE:
<223> OTHER INFORMATION: Partial peptide of BMP-6

<400> SEQUENCE: 19

Tyr Val Pro Lys Pro Cys Cys Ala Pro Thr Lys Leu Asn Ala Ile Ser
1               5                   10                  15

Val Leu Tyr Phe
            20

<210> SEQ ID NO 20
<211> LENGTH: 24
<212> TYPE: PRT
<213> ORGANISM: Artificial Sequence
```

```
<220> FEATURE:
<223> OTHER INFORMATION: Partial peptide of BMP-6

<400> SEQUENCE: 20

Ser Val Leu Tyr Phe Asp Asp Asn Ser Asn Val Ile Leu Lys Lys Tyr
1               5                   10                  15

Arg Asn Met Val Val Arg Ala Cys
            20

<210> SEQ ID NO 21
<211> LENGTH: 20
<212> TYPE: PRT
<213> ORGANISM: Artificial Sequence
<220> FEATURE:
<223> OTHER INFORMATION: Partial sequence of BMP-7

<400> SEQUENCE: 21

Thr Val Pro Lys Pro Cys Cys Ala Pro Thr Gln Leu Asn Ala Ile Ser
1               5                   10                  15

Val Leu Tyr Phe
            20

<210> SEQ ID NO 22
<211> LENGTH: 21
<212> TYPE: PRT
<213> ORGANISM: Artificial Sequence
<220> FEATURE:
<223> OTHER INFORMATION: Partial peptide of BMP-7

<400> SEQUENCE: 22

Glu Asn Ser Ser Ser Asp Gln Arg Gln Ala Cys Lys Lys His Glu Leu
1               5                   10                  15

Tyr Val Ser Phe Arg
            20

<210> SEQ ID NO 23
<211> LENGTH: 20
<212> TYPE: PRT
<213> ORGANISM: Artificial Sequence
<220> FEATURE:
<223> OTHER INFORMATION: Partial peptide of BMP-7

<400> SEQUENCE: 23

Thr Val Pro Lys Pro Cys Cys Ala Pro Thr Gln Leu Asn Ala Ile Ser
1               5                   10                  15

Val Leu Tyr Phe
            20

<210> SEQ ID NO 24
<211> LENGTH: 19
<212> TYPE: PRT
<213> ORGANISM: Artificial Sequence
<220> FEATURE:
<223> OTHER INFORMATION: Partial peptide of BMP-7

<400> SEQUENCE: 24

Ser Val Leu Tyr Phe Asp Asp Ser Ser Asn Val Ile Leu Lys Lys Tyr
1               5                   10                  15

Arg Asn Met

<210> SEQ ID NO 25
<211> LENGTH: 8
<212> TYPE: PRT
<213> ORGANISM: Artificial Sequence
<220> FEATURE:
```

<223> OTHER INFORMATION: Partial peptide of bone sialoprotein

<400> SEQUENCE: 25

Glu Glu Glu Gly Glu Glu Glu Glu
1               5

<210> SEQ ID NO 26
<211> LENGTH: 10
<212> TYPE: PRT
<213> ORGANISM: Artificial Sequence
<220> FEATURE:
<223> OTHER INFORMATION: Partial peptide of bone sialoprotein

<400> SEQUENCE: 26

Glu Glu Glu Glu Glu Glu Glu Glu Glu Glu
1               5                   10

<210> SEQ ID NO 27
<211> LENGTH: 18
<212> TYPE: PRT
<213> ORGANISM: Artificial Sequence
<220> FEATURE:
<223> OTHER INFORMATION: Partial peptide of bone sialoprotein

<400> SEQUENCE: 27

Tyr Glu Thr Tyr Asp Glu Asn Asn Gly Glu Pro Arg Gly Asp Thr Tyr
1               5                   10                  15

Arg Ile

<210> SEQ ID NO 28
<211> LENGTH: 6
<212> TYPE: PRT
<213> ORGANISM: Artificial Sequence
<220> FEATURE:
<223> OTHER INFORMATION: Partial peptide of bone sialoprotein

<400> SEQUENCE: 28

Glu Glu Gly Glu Glu Glu
1               5

<210> SEQ ID NO 29
<211> LENGTH: 8
<212> TYPE: PRT
<213> ORGANISM: Artificial Sequence
<220> FEATURE:
<223> OTHER INFORMATION: Partial peptide of bone sialoprotein

<400> SEQUENCE: 29

Glu Glu Glu Glu Glu Glu Glu Glu
1               5

<210> SEQ ID NO 30
<211> LENGTH: 17
<212> TYPE: PRT
<213> ORGANISM: Artificial Sequence
<220> FEATURE:
<223> OTHER INFORMATION: Partial peptide of bone sialoprotein

<400> SEQUENCE: 30

Tyr Glu Ile Tyr Glu Ser Glu Asn Gly Glu Pro Arg Gly Asp Asn Tyr
1               5                   10                  15

Arg

<210> SEQ ID NO 31
<211> LENGTH: 9
<212> TYPE: PRT

```
<213> ORGANISM: Artificial Sequence
<220> FEATURE:
<223> OTHER INFORMATION: Partial peptide of bone sialoprotein

<400> SEQUENCE: 31

Lys Asn Leu His Arg Arg Val Lys Ile
1               5

<210> SEQ ID NO 32
<211> LENGTH: 26
<212> TYPE: PRT
<213> ORGANISM: Artificial Sequence
<220> FEATURE:
<223> OTHER INFORMATION: Partial peptide of bone sialoprotein

<400> SEQUENCE: 32

Asp Ser Ser Glu Glu Asn Gly Asp Asp Ser Glu Glu Glu Glu Glu Glu
1               5                   10                  15

Glu Glu Glu Thr Ser Asn Glu Gly Glu Asn
            20                  25

<210> SEQ ID NO 33
<211> LENGTH: 21
<212> TYPE: PRT
<213> ORGANISM: Artificial Sequence
<220> FEATURE:
<223> OTHER INFORMATION: Partial peptide of bone sialoprotein

<400> SEQUENCE: 33

Asp Glu Glu Glu Glu Glu Glu Glu Gly Asn Glu Asn Glu Glu Ser
1               5                   10                  15

Glu Ala Glu Val Asp
            20

<210> SEQ ID NO 34
<211> LENGTH: 11
<212> TYPE: PRT
<213> ORGANISM: Artificial Sequence
<220> FEATURE:
<223> OTHER INFORMATION: Partial peptide of bone sialoprotein

<400> SEQUENCE: 34

Ser Glu Asn Gly Glu Pro Arg Gly Asp Asn Tyr
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Partial peptide of TGF

<400> SEQUENCE: 35

Thr Gly Arg Arg Gly Asp Leu Ala Thr
1               5

<210> SEQ ID NO 36
<211> LENGTH: 21
<212> TYPE: PRT
<213> ORGANISM: Artificial Sequence
<220> FEATURE:
<223> OTHER INFORMATION: Partial peptide of TGF

<400> SEQUENCE: 36

Arg Ala Leu Asp Thr Asn Tyr Cys Phe Ser Ser Thr Glu Lys Asn Cys
1               5                   10                  15
```

```
Cys Val Arg Gln Leu
            20

<210> SEQ ID NO 37
<211> LENGTH: 19
<212> TYPE: PRT
<213> ORGANISM: Artificial Sequence
<220> FEATURE:
<223> OTHER INFORMATION: Partial peptide of TGF

<400> SEQUENCE: 37

Leu Tyr Asn Gln His Asn Pro Gly Ala Ser Ala Ala Pro Cys Cys Val
1               5                   10                  15

Pro Gln Ala

<210> SEQ ID NO 38
<211> LENGTH: 21
<212> TYPE: PRT
<213> ORGANISM: Artificial Sequence
<220> FEATURE:
<223> OTHER INFORMATION: Partial peptide of PDGF

<400> SEQUENCE: 38

Cys Glu Thr Val Ala Ala Ala Arg Pro Val Thr Arg Ser Pro Gly Gly
1               5                   10                  15

Ser Gln Glu Gln Arg
            20

<210> SEQ ID NO 39
<211> LENGTH: 20
<212> TYPE: PRT
<213> ORGANISM: Artificial Sequence
<220> FEATURE:
<223> OTHER INFORMATION: Partial peptide of PDGF

<400> SEQUENCE: 39

Ala Lys Thr Pro Gln Thr Arg Val Thr Ile Arg Thr Val Arg Val Arg
1               5                   10                  15

Arg Pro Pro Lys
            20

<210> SEQ ID NO 40
<211> LENGTH: 9
<212> TYPE: PRT
<213> ORGANISM: Artificial Sequence
<220> FEATURE:
<223> OTHER INFORMATION: Partial peptide of AFGF

<400> SEQUENCE: 40

Tyr Lys Lys Pro Lys Leu Leu Tyr Cys
1               5

<210> SEQ ID NO 41
<211> LENGTH: 8
<212> TYPE: PRT
<213> ORGANISM: Artificial Sequence
<220> FEATURE:
<223> OTHER INFORMATION: Partial peptide of AFGF

<400> SEQUENCE: 41

Ile Ser Lys Lys His Ala Glu Lys
1               5

<210> SEQ ID NO 42
<211> LENGTH: 12
<212> TYPE: PRT
```

```
<213> ORGANISM: Artificial Sequence
<220> FEATURE:
<223> OTHER INFORMATION: Partial peptide of BFGF

<400> SEQUENCE: 42

Gly His Phe Lys Asp Pro Lys Arg Leu Tyr Cys Lys
1               5                   10

<210> SEQ ID NO 43
<211> LENGTH: 6
<212> TYPE: PRT
<213> ORGANISM: Artificial Sequence
<220> FEATURE:
<223> OTHER INFORMATION: Partial peptide of BFGF

<400> SEQUENCE: 43

Pro Asp Gly Arg Val Asp
1               5

<210> SEQ ID NO 44
<211> LENGTH: 7
<212> TYPE: PRT
<213> ORGANISM: Artificial Sequence
<220> FEATURE:
<223> OTHER INFORMATION: Partial peptide of BFGF

<400> SEQUENCE: 44

Lys Glu Asp Gly Arg Leu Leu
1               5

<210> SEQ ID NO 45
<211> LENGTH: 6
<212> TYPE: PRT
<213> ORGANISM: Artificial Sequence
<220> FEATURE:
<223> OTHER INFORMATION: Partial peptide of BFGF

<400> SEQUENCE: 45

Tyr Arg Ser Arg Lys Tyr
1               5

<210> SEQ ID NO 46
<211> LENGTH: 21
<212> TYPE: PRT
<213> ORGANISM: Artificial Sequence
<220> FEATURE:
<223> OTHER INFORMATION: Partial peptide of dentin sialoprotein

<400> SEQUENCE: 46

Glu Asp Glu Gly Ser Gly Asp Asp Glu Asp Glu Ala Gly Asn Gly
1               5                   10                  15

Lys Asp Ser Ser Asn
            20

<210> SEQ ID NO 47
<211> LENGTH: 20
<212> TYPE: PRT
<213> ORGANISM: Artificial Sequence
<220> FEATURE:
<223> OTHER INFORMATION: Partial peptide of dentin sialoprotein

<400> SEQUENCE: 47

Asp Asp Ala Asn Ser Glu Ser Asp Asn Asn Ser Ser Arg Gly Asp
1               5                   10                  15

Ala Ser Tyr Asn
            20
```

```
<210> SEQ ID NO 48
<211> LENGTH: 23
<212> TYPE: PRT
<213> ORGANISM: Artificial Sequence
<220> FEATURE:
<223> OTHER INFORMATION: Partial peptide of dentin sialoprotein

<400> SEQUENCE: 48

Asp Ser Asp Ser Ser Asp Ser Ser Asn Ser Ser Asp Ser Ser Asp Ser
1               5                   10                  15

Ser Asp Ser Asp Ser Ser Asp
            20

<210> SEQ ID NO 49
<211> LENGTH: 22
<212> TYPE: PRT
<213> ORGANISM: Artificial Sequence
<220> FEATURE:
<223> OTHER INFORMATION: Partial peptide of heparin binding EGF like GF

<400> SEQUENCE: 49

Asp Leu Gln Glu Ala Asp Leu Ala Leu Leu Arg Val Thr Leu Ser Ser
1               5                   10                  15

Lys Pro Gln Ala Leu Ala
            20

<210> SEQ ID NO 50
<211> LENGTH: 20
<212> TYPE: PRT
<213> ORGANISM: Artificial Sequence
<220> FEATURE:
<223> OTHER INFORMATION: Partial peptide of heparin binding EGF like GF

<400> SEQUENCE: 50

Ala Thr Pro Asn Lys Glu Glu His Gly Lys Arg Lys Lys Lys Gly Lys
1               5                   10                  15

Gly Leu Gly Lys
            20

<210> SEQ ID NO 51
<211> LENGTH: 13
<212> TYPE: PRT
<213> ORGANISM: Artificial Sequence
<220> FEATURE:
<223> OTHER INFORMATION: Partial peptide of heparin binding EGF like GF

<400> SEQUENCE: 51

Lys Arg Asp Pro Cys Leu Arg Lys Tyr Lys Asp Phe Cys
1               5                   10

<210> SEQ ID NO 52
<211> LENGTH: 20
<212> TYPE: PRT
<213> ORGANISM: Artificial Sequence
<220> FEATURE:
<223> OTHER INFORMATION: Partial peptide of heparin binding EGF like GF

<400> SEQUENCE: 52

Cys Lys Tyr Val Lys Glu Leu Arg Ala Pro Ser Cys Ile Cys His Pro
1               5                   10                  15

Gly Tyr His Gly
            20

<210> SEQ ID NO 53
<211> LENGTH: 25
```

```
<212> TYPE: PRT
<213> ORGANISM: Artificial Sequence
<220> FEATURE:
<223> OTHER INFORMATION: Partial peptide of cadherin EGF LAG seven-pass
      G-type receptor3

<400> SEQUENCE: 53

Pro Gln Tyr Asn Tyr Gln Thr Leu Val Pro Glu Asn Glu Ala Ala Gly
1               5                   10                  15

Thr Ala Val Leu Arg Val Val Ala Gln
            20                  25

<210> SEQ ID NO 54
<211> LENGTH: 21
<212> TYPE: PRT
<213> ORGANISM: Artificial Sequence
<220> FEATURE:
<223> OTHER INFORMATION: Partial peptide of cadherin EGF LAG seven-pass
      G-type receptor3

<400> SEQUENCE: 54

Asp Pro Asp Ala Gly Glu Ala Gly Arg Leu Val Tyr Ser Leu Ala Ala
1               5                   10                  15

Leu Met Asn Ser Arg
            20

<210> SEQ ID NO 55
<211> LENGTH: 29
<212> TYPE: PRT
<213> ORGANISM: Artificial Sequence
<220> FEATURE:
<223> OTHER INFORMATION: Partial sequence of cadherin EGF LAG seven-pass
      G-type receptor3

<400> SEQUENCE: 55

Ser Leu Glu Leu Phe Ser Ile Asp Pro Gln Ser Gly Leu Ile Arg Thr
1               5                   10                  15

Ala Ala Ala Leu Asp Arg Glu Ser Met Glu Arg His Tyr
            20                  25

<210> SEQ ID NO 56
<211> LENGTH: 23
<212> TYPE: PRT
<213> ORGANISM: Artificial Sequence
<220> FEATURE:
<223> OTHER INFORMATION: Partial peptide of cadherin EGF LAG seven-pass
      G-type receptor3

<400> SEQUENCE: 56

Leu Arg Val Thr Ala Gln Asp His Gly Ser Pro Arg Leu Ser Ala Thr
1               5                   10                  15

Thr Met Val Ala Val Thr Val
            20

<210> SEQ ID NO 57
<211> LENGTH: 112
<212> TYPE: PRT
<213> ORGANISM: Artificial Sequence
<220> FEATURE:
<223> OTHER INFORMATION: Partial peptide of cadherin EGF LAG seven-pass
      G-type receptor3

<400> SEQUENCE: 57

Glu Gln Ala Gln Tyr Arg Glu Thr Leu Arg Glu Asn Val Glu Glu Gly
1               5                   10                  15

Tyr Pro Ile Leu Gln Leu Arg Ala Thr Asp Gly Asp Ala Pro Pro Asn
```

```
                    20                  25                  30

Ala Asn Leu Arg Tyr Arg Phe Val Gly Pro Pro Ala Ala Arg Ala Ala
            35                  40                  45

Ala Ala Ala Ala Phe Glu Ile Asp Pro Arg Ser Gly Leu Ile Ser Thr
    50                  55                  60

Ser Gly Arg Val Asp Arg Glu His Met Glu Ser Tyr Glu Leu Val Val
65                  70                  75                  80

Glu Ala Ser Asp Gln Gly Gln Glu Pro Gly Pro Arg Ser Ala Thr Val
                85                  90                  95

Arg Val His Ile Thr Val Leu Asp Glu Asn Asp Asn Ala Pro Gln Phe
                100                 105                 110

<210> SEQ ID NO 58
<211> LENGTH: 106
<212> TYPE: PRT
<213> ORGANISM: Artificial Sequence
<220> FEATURE:
<223> OTHER INFORMATION: Partial peptide of cadherin EGF LAG seven-pass
      G-type receptor3

<400> SEQUENCE: 58

Ser Glu Lys Arg Tyr Val Ala Gln Val Arg Glu Asp Val Arg Pro His
1               5                   10                  15

Thr Val Val Leu Arg Val Thr Ala Thr Asp Arg Asp Lys Asp Ala Asn
                20                  25                  30

Gly Leu Val His Tyr Asn Ile Ile Ser Gly Asn Ser Arg Gly His Phe
            35                  40                  45

Ala Ile Asp Ser Leu Thr Gly Glu Ile Gln Val Val Ala Pro Leu Asp
    50                  55                  60

Phe Glu Ala Glu Arg Glu Tyr Ala Leu Arg Ile Arg Ala Gln Asp Ala
65                  70                  75                  80

Gly Arg Pro Pro Leu Ser Asn Asn Thr Gly Leu Ala Ser Ile Gln Val
                85                  90                  95

Val Asp Ile Asn Asp His Ile Pro Ile Phe
                100                 105

<210> SEQ ID NO 59
<211> LENGTH: 59
<212> TYPE: PRT
<213> ORGANISM: Artificial Sequence
<220> FEATURE:
<223> OTHER INFORMATION: Partial peptide of cadherin EGF LAG seven-pass
      G-type receptor3

<400> SEQUENCE: 59

Asp Asp Asn Val Cys Leu Arg Glu Pro Cys Glu Asn Tyr Met Lys Cys
1               5                   10                  15

Val Ser Val Leu Arg Phe Asp Ser Ser Ala Pro Phe Leu Ala Ser Ala
                20                  25                  30

Ser Thr Leu Phe Arg Pro Ile Gln Pro Ile Ala Gly Leu Arg Cys Arg
            35                  40                  45

Cys Pro Pro Gly Phe Thr Gly Asp Phe Cys Glu
    50                  55

<210> SEQ ID NO 60
<211> LENGTH: 37
<212> TYPE: PRT
<213> ORGANISM: Artificial Sequence
<220> FEATURE:
<223> OTHER INFORMATION: Partial peptide of cadherin EGF LAG seven-pass
      G-type receptor3
```

```
<400> SEQUENCE: 60

Glu Leu Asp Leu Cys Tyr Ser Asn Pro Cys Arg Asn Gly Gly Ala Cys
1               5                   10                  15

Ala Arg Arg Glu Gly Gly Tyr Thr Cys Val Cys Arg Pro Arg Phe Thr
            20                  25                  30

Gly Glu Asp Cys Glu
        35

<210> SEQ ID NO 61
<211> LENGTH: 40
<212> TYPE: PRT
<213> ORGANISM: Artificial Sequence
<220> FEATURE:
<223> OTHER INFORMATION: Partial peptide of cadherin EGF LAG seven-pass
      G-type receptor3

<400> SEQUENCE: 61

Glu Ala Gly Arg Cys Val Pro Gly Val Cys Asn Gly Gly Thr Cys
1               5                   10                  15

Thr Asp Ala Pro Asn Gly Gly Phe Arg Cys Gln Cys Pro Ala Gly Gly
            20                  25                  30

Ala Phe Glu Gly Pro Arg Cys Glu
        35                  40

<210> SEQ ID NO 62
<211> LENGTH: 205
<212> TYPE: PRT
<213> ORGANISM: Artificial Sequence
<220> FEATURE:
<223> OTHER INFORMATION: Partial peptide of cadherin EGF LAG seven-pass
      G-type receptor3

<400> SEQUENCE: 62

Val Ala Ala Arg Ser Phe Pro Pro Ser Ser Phe Val Met Phe Arg Gly
1               5                   10                  15

Leu Arg Gln Arg Phe His Leu Thr Leu Ser Leu Ser Phe Ala Thr Val
            20                  25                  30

Gln Gln Ser Gly Leu Leu Phe Tyr Asn Gly Arg Leu Asn Glu Lys His
        35                  40                  45

Asp Phe Leu Ala Leu Glu Leu Val Ala Gly Gln Val Arg Leu Thr Tyr
    50                  55                  60

Ser Thr Gly Glu Ser Asn Thr Val Val Ser Pro Thr Val Pro Gly Gly
65                  70                  75                  80

Leu Ser Asp Gly Gln Trp His Thr Val His Leu Arg Tyr Tyr Asn Lys
                85                  90                  95

Pro Arg Thr Asp Ala Leu Gly Gly Ala Gln Gly Pro Ser Lys Asp Lys
            100                 105                 110

Val Ala Val Leu Ser Val Asp Asp Cys Asp Val Ala Val Ala Leu Gln
        115                 120                 125

Phe Gly Ala Glu Ile Gly Asn Tyr Ser Cys Ala Ala Ala Gly Val Gln
    130                 135                 140

Thr Ser Ser Lys Lys Ser Leu Asp Leu Thr Gly Pro Leu Leu Leu Gly
145                 150                 155                 160

Gly Val Pro Asn Leu Pro Glu Asn Phe Pro Val Ser His Lys Asp Phe
                165                 170                 175

Ile Gly Cys Met Arg Asp Leu His Ile Asp Gly Arg Arg Val Asp Met
            180                 185                 190

Ala Ala Phe Val Ala Asn Asn Gly Thr Met Ala Gly Cys
```

195         200         205

<210> SEQ ID NO 63
<211> LENGTH: 181
<212> TYPE: PRT
<213> ORGANISM: Artificial Sequence
<220> FEATURE:
<223> OTHER INFORMATION: Partial peptide of cadherin EGF LAG seven-pass
      G-type receptor3

<400> SEQUENCE: 63

Pro His His Phe Arg Gly Asn Gly Thr Leu Ser Trp Asn Phe Gly Ser
1               5                   10                  15

Asp Met Ala Val Ser Val Pro Trp Tyr Leu Gly Leu Ala Phe Arg Thr
            20                  25                  30

Arg Ala Thr Gln Gly Val Leu Met Gln Val Gln Ala Gly Pro His Ser
        35                  40                  45

Thr Leu Leu Cys Gln Leu Asp Arg Gly Leu Leu Ser Val Thr Val Thr
    50                  55                  60

Arg Gly Ser Gly Arg Ala Ser His Leu Leu Asp Gln Val Thr Val
65                  70                  75                  80

Ser Asp Gly Arg Trp His Asp Leu Arg Leu Glu Leu Gln Glu Glu Pro
                85                  90                  95

Gly Gly Arg Arg Gly His His Val Leu Met Val Ser Leu Asp Phe Ser
            100                 105                 110

Leu Phe Gln Asp Thr Met Ala Val Gly Ser Glu Leu Gln Gly Leu Lys
        115                 120                 125

Val Lys Gln Leu His Val Gly Gly Leu Pro Pro Gly Ser Ala Glu Glu
    130                 135                 140

Ala Pro Gln Gly Leu Val Gly Cys Ile Gln Gly Val Trp Leu Gly Ser
145                 150                 155                 160

Thr Pro Ser Gly Ser Pro Ala Leu Leu Pro Ser His Arg Val Asn
                165                 170                 175

Ala Glu Pro Gly Cys
            180

<210> SEQ ID NO 64
<211> LENGTH: 36
<212> TYPE: PRT
<213> ORGANISM: Artificial Sequence
<220> FEATURE:
<223> OTHER INFORMATION: Partial peptide of cadherin EGF LAG seven-pass
      G-type receptor3

<400> SEQUENCE: 64

Cys Pro Cys Arg Pro Gly Ala Leu Gly Arg Gln Cys Asn Ser Cys Asp
1               5                   10                  15

Ser Pro Phe Ala Glu Val Thr Ala Ser Gly Cys Arg Val Leu Tyr Asp
            20                  25                  30

Ala Cys Pro Lys
        35

<210> SEQ ID NO 65
<211> LENGTH: 106
<212> TYPE: PRT
<213> ORGANISM: Artificial Sequence
<220> FEATURE:
<223> OTHER INFORMATION: Partial peptide of OB-cadherin

<400> SEQUENCE: 65

Gly Trp Val Trp Asn Gln Phe Phe Val Ile Gly Gly Tyr Thr Gly Pro

```
                  1               5                  10                 15
Asp Pro Val Leu Val Gly Arg Leu His Ser Asp Ile Asp Ser Gly Asp
                 20                 25                 30

Gly Asn Ile Lys Tyr Ile Leu Ser Gly Glu Gly Ala Gly Thr Ile Phe
                 35                 40                 45

Val Ile Asp Asp Lys Ser Gly Asn Ile His Ala Thr Lys Thr Leu Asp
 50                 55                 60

Arg Glu Glu Arg Ala Gln Tyr Thr Leu Met Ala Gln Ala Val Asp Arg
 65                 70                 75                 80

Asp Thr Asn Arg Pro Leu Glu Pro Pro Ser Glu Phe Ile Val Lys Val
                 85                 90                 95

Gln Asp Ile Asn Asp Asn Pro Pro Glu Phe
                100                105

<210> SEQ ID NO 66
<211> LENGTH: 109
<212> TYPE: PRT
<213> ORGANISM: Artificial Sequence
<220> FEATURE:
<223> OTHER INFORMATION: Partial peptide of OB-cadherin

<400> SEQUENCE: 66

Leu His Glu Thr Tyr His Ala Asn Val Pro Glu Arg Ser Asn Val Gly
 1               5                  10                 15

Thr Ser Val Ile Gln Val Thr Ala Ser Asp Ala Asp Asp Pro Thr Tyr
                 20                 25                 30

Gly Asn Ser Ala Lys Leu Val Tyr Ser Ile Leu Glu Gly Gln Pro Tyr
                 35                 40                 45

Phe Ser Val Glu Ala Gln Thr Gly Ile Ile Arg Thr Ala Leu Pro Asn
 50                 55                 60

Met Asp Arg Glu Ala Lys Glu Glu Tyr His Val Val Ile Gln Ala Lys
 65                 70                 75                 80

Asp Met Gly Gly His Met Gly Gly Leu Ser Gly Thr Thr Lys Val Thr
                 85                 90                 95

Ile Thr Leu Thr Asp Val Asn Asp Asn Pro Pro Lys Phe
                100                105

<210> SEQ ID NO 67
<211> LENGTH: 115
<212> TYPE: PRT
<213> ORGANISM: Artificial Sequence
<220> FEATURE:
<223> OTHER INFORMATION: Partial peptide of OB-cadherin

<400> SEQUENCE: 67

Pro Gln Arg Leu Tyr Gln Met Ser Val Ser Glu Ala Ala Val Pro Gly
 1               5                  10                 15

Glu Glu Val Gly Arg Val Lys Ala Lys Asp Pro Asp Ile Gly Glu Asn
                 20                 25                 30

Gly Leu Val Thr Tyr Asn Ile Val Asp Gly Asp Gly Met Glu Ser Phe
                 35                 40                 45

Glu Ile Thr Thr Asp Tyr Glu Thr Gln Glu Gly Val Ile Lys Leu Lys
 50                 55                 60

Lys Pro Val Asp Phe Glu Thr Glu Arg Ala Tyr Ser Leu Lys Val Glu
 65                 70                 75                 80

Ala Ala Asn Val His Ile Asp Pro Lys Phe Ile Ser Asn Gly Pro Phe
                 85                 90                 95

Lys Asp Thr Val Thr Val Lys Ile Ser Val Glu Asp Ala Asp Glu Pro
```

```
                        100             105              110
Pro Met Phe
            115

<210> SEQ ID NO 68
<211> LENGTH: 106
<212> TYPE: PRT
<213> ORGANISM: Artificial Sequence
<220> FEATURE:
<223> OTHER INFORMATION: Partial peptide of OB-cadherin

<400> SEQUENCE: 68

Pro Met Phe Leu Ala Pro Ser Tyr Ile His Glu Val Gln Glu Asn Ala
1               5                   10                  15

Ala Ala Gly Thr Val Val Gly Arg Val His Ala Lys Asp Pro Asp Ala
            20                  25                  30

Ala Asn Ser Pro Ile Arg Trp Ser Ile Asp Arg His Thr Asp Leu Asp
        35                  40                  45

Arg Phe Phe Thr Ile Asn Pro Glu Asp Gly Phe Ile Lys Thr Thr Lys
    50                  55                  60

Pro Leu Asp Arg Glu Glu Thr Ala Trp Leu Asn Ile Thr Val Phe Ala
65                  70                  75                  80

Ala Glu Ile His Asn Arg His Gln Glu Ala Gln Val Pro Val Ala Ile
                85                  90                  95

Arg Val Leu Asp Val Asn Asp Asn Ala Pro
            100                 105

<210> SEQ ID NO 69
<211> LENGTH: 126
<212> TYPE: PRT
<213> ORGANISM: Artificial Sequence
<220> FEATURE:
<223> OTHER INFORMATION: Partial peptide of OB-cadherin

<400> SEQUENCE: 69

Lys Phe Ala Ala Pro Tyr Glu Gly Phe Ile Cys Glu Ser Asp Gln Thr
1               5                   10                  15

Lys Pro Leu Ser Asn Gln Pro Ile Val Thr Ile Ser Ala Asp Asp Lys
            20                  25                  30

Asp Asp Thr Ala Asn Gly Pro Arg Phe Ile Phe Ser Leu Pro Pro Gly
        35                  40                  45

Ile Ile His Asn Pro Asn Phe Thr Val Arg Asp Asn Arg Asp Asn Thr
    50                  55                  60

Ala Gly Val Tyr Ala Arg Arg Gly Gly Phe Ser Arg Gln Lys Gln Asp
65                  70                  75                  80

Leu Tyr Leu Leu Pro Ile Val Ile Ser Asp Gly Gly Ile Pro Pro Met
                85                  90                  95

Ser Ser Thr Asn Thr Leu Thr Ile Leu Val Cys Gly Cys Asp Val Asn
            100                 105                 110

Gly Ala Leu Leu Ser Cys Asn Ala Glu Ala Tyr Ile Leu Asn
        115                 120                 125
```